US012693296B2

(12) United States Patent
Zuk et al.

(10) Patent No.: US 12,693,296 B2
(45) Date of Patent: Jul. 28, 2026

(54) METHOD FOR DETERMINING ANTIBODY DISSOCIATION RATE

(71) Applicant: Access Medical Systems, Ltd., Palo Alto, CA (US)

(72) Inventors: Robert F. Zuk, Menlo Park, CA (US); Mohsen Karbaschi, Santa Clara, CA (US); Heng Wu, Shanghai (CN); Haode Chen, Shanghai (CN)

(73) Assignee: ACCESS MEDICAL SYSTEMS, LTD., Palo Alto, CA (US)

( * ) Notice: Subject to any disclaimer, the term of this patent is extended or adjusted under 35 U.S.C. 154(b) by 905 days.

(21) Appl. No.: 18/061,893

(22) Filed: Dec. 5, 2022

(65) Prior Publication Data

US 2023/0104035 A1 Apr. 6, 2023

Related U.S. Application Data

(63) Continuation of application No. PCT/US2021/035665, filed on Jun. 3, 2021.

(60) Provisional application No. 63/139,608, filed on Jan. 20, 2021, provisional application No. 63/035,507, filed on Jun. 5, 2020.

(51) Int. Cl.
| | |
|---|---|
| *G01N 33/58* | (2006.01) |
| *C07K 16/104* | (2026.01) |
| *G01N 21/64* | (2006.01) |
| *G01N 33/543* | (2006.01) |
| *G01N 33/557* | (2006.01) |

(52) U.S. Cl.
CPC ......... *G01N 33/582* (2013.01); *C07K 16/104* (2026.01); *G01N 21/6428* (2013.01); *G01N 33/543* (2013.01); *G01N 33/557* (2013.01); *G01N 2021/6439* (2013.01)

(58) Field of Classification Search
CPC .............. G01N 33/557; G01N 33/582; C07K 2317/92; C07K 16/104
USPC ........................................................ 436/517
See application file for complete search history.

(56) References Cited

U.S. PATENT DOCUMENTS

| | | | |
|---|---|---|---|
| 2018/0180606 A1* | 6/2018 | Zuk | G01N 33/533 |
| 2018/0258469 A1* | 9/2018 | Johnson-Buck | |
| | | | G01N 33/54306 |

OTHER PUBLICATIONS

Wu, et al, "A new coronavirus associated with human respiratory disease in China", Nature, Feb. 3, 2020, vol. 579, No. 7798, pp. 265-269.

Sempowski, et al, "Pandemic preparedness: developing vaccines and therapeutic antibodies 9 for COVID-19.", Cell, May 27, 2020, vol. 181, No. 7, pp. 1-8.

United States Patent & Trademark Office (USPTO), International Search Report (ISR), PCT/US2021/035665, Oct. 1, 2021.

European Patent Office (EPO), Extended European Search Report (EESR), EP No. 21818008.1, Jun. 3, 2024.

Yang, et al, "SARS-CoV-2 antibody characterization in emergency department, hospitalized and convalescent patients by two semi-quantitative immunoassays", Clinica Chimica Acta, Elsevier B.V., Amsterdam, NL, vol. 509, Jun. 4, 2020, pp. 117-125.

Concepcion, et al, "Label-free detection of biomolecular interactions using BioLayer interferometry for kinetic characterization", Combinatorial Chemistry and High Throughput Screening, Bentham Science Publishers, NL, vol. 12, No. 8, Sep. 1, 2009.

* cited by examiner

*Primary Examiner* — Gregory S Emch
*Assistant Examiner* — Omar Ramadan
(74) *Attorney, Agent, or Firm* — Perkins Coie LLP; Viola T. Kung

(57) ABSTRACT

The present invention is directed to a method of measuring the dissociation rate of the binding of an antibody to an antigen. The method has two phases: a first phase of binding and a second phase of dissociation. The first phase of the assay has a probe coated with an antigen, or protein G, or an anti-human IgG Fc antibody. The probe is immersed in a sample solution containing an antibody, followed by a wash sequence, then the probe is transferred to a reagent with a biotinylated antigen. After an incubation, the antibody bound on the probe binds to the biotinylated antigen to form an immune complex. Fluorescent signal is produced by immersing the probe in a reagent having a fluorescent tagged streptavidin. The last step of the first phase is a measurement of fluorescent on the probe tip. The second phase of the assay is making subsequent fluorescent measurements over time to monitor the loss in fluorescence indicating dissociation of the immune complex and calculating the dissociation rate of the binding of the antibody to the antigen.

17 Claims, 10 Drawing Sheets

Cy5-SA Monomer Disassociation Rate

| AB # | Pylon-Cy5-SA monomer Dissociation Rate [1/s] | Gator koff(1/s) |
|---|---|---|
| 1 | 4.30E-04 | 5.69E-05 |
| 2 | 5.57E-04 | 1.13E-04 |
| 3 | 7.42E-04 | 1.22E-04 |
| 4 | 9.75E-04 | 1.75E-04 |
| 5 | 1.08E-03 | 1.62E-04 |
| 6 | 1.20E-03 | 1.61E-04 |
| 7 | 1.36E-03 | 2.85E-04 |
| 8 | 1.43E-03 | 1.01E-03 |

Figure 8:
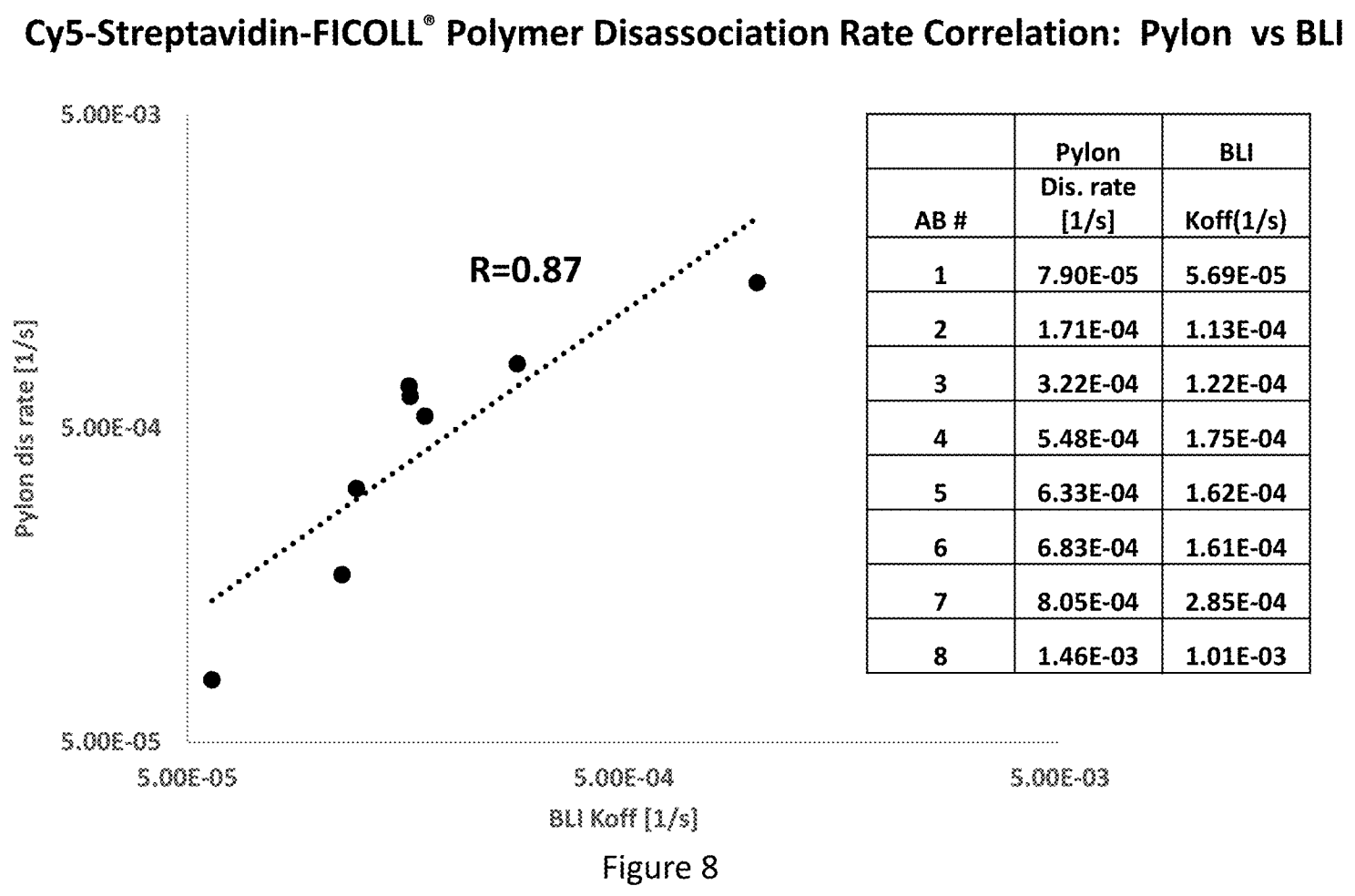

Cy5-Streptavidin-FICOLL® Polymer Disassociation Rate Correlation: Pylon vs BLI

| AB # | Pylon Dis. rate [1/s] | BLI Koff(1/s) |
|------|------------------------|----------------|
| 1 | 7.90E-05 | 5.69E-05 |
| 2 | 1.71E-04 | 1.13E-04 |
| 3 | 3.22E-04 | 1.22E-04 |
| 4 | 5.48E-04 | 1.75E-04 |
| 5 | 6.33E-04 | 1.62E-04 |
| 6 | 6.83E-04 | 1.61E-04 |
| 7 | 8.05E-04 | 2.85E-04 |
| 8 | 1.46E-03 | 1.01E-03 |

METHOD FOR DETERMINING ANTIBODY DISSOCIATION RATE

This application is a continuation of PCT/US2021/035665, filed Jun. 3, 2021; which claims the benefit of U.S. Provisional Application Nos. 63/035,507, filed Jun. 5, 2020, and 63/139,608, filed Jan. 20, 2021. The contents of the above-identified applications are incorporated herein by reference in their entireties.

FIELD OF THE INVENTION

The present invention related to an immunoassay method to determine the dissociation rate of an antibody.

BACKGROUND OF THE INVENTION

Evaluating the immune response to pathogens is a critical aspect in management of infectious disease. Many aspects of the immunoglobulin response have been well studied such as immunoglobulin type, IgG subclass, neutralizing antibody, and titer maturation over time. One aspect of characterizing the basic binding between antibody and antigen is affinity. There are methods to measure the association rate of the immune complex formation, followed by monitoring the dissociation rate of the immune complex to derive an overall equilibrium binding constant. Label-free analytical methods such as BioLayer Interferometry (BLI, Comb Chem High Throughput Screen, 2009 September; 12(8):791-800) offers an advantage of determining antibody affinity without the use of labels that could perturb the immune binding. Ylera et al. (Analytical Biochemistry 441 (2013) 208-213) report-off-rate screening for selection of high-affinity anti-drug antibodies using BLI method. These methods have become the accepted gold standard for affinity measurements. BLI has been widely used in biotherapeutic development, however, the lack of sensitivity and potential interference by crude biological samples have restricted clinical applications.

Label-free methods are most commonly applied to characterize affinity of monoclonal antibodies, however, the immune response to pathogens is heterogenous with polyclonal antibodies involving different immunoglobulin types, IgG, IgM and IgA. In the characterization of antibody binding in clinical samples, the term avidity is more appropriate. Avidity is associated with the combination of binding affinity and multiple antibody binding sites. For example, IgG has 2 binding sites while IgM has 10 binding sites due to its pentameric structure. IgM typically has lower affinity compared to IgG, but has high avidity.

There are examples of solid phase assays with conventional labels (Clinical and Vaccine Immunology, Fed 2013, v20, #2, 197-800) applied for distinguishing acute versus chronic toxoplasmosis infections using the assumption that avidity increases as the immune response matures in the prolonged chronic infection. The methods employ a denaturation reagent, 6M urea, to disassociate the immune complex on the solid phase. Antibody samples more tolerant of the denaturation step are designated as higher avidity from a chronic infection because of the longer time for maturation of the immune response. These methods have limitations in that the binding under denaturation conditions does not necessarily correspond to the binding avidity under physiologic conditions. Secondly, a reference test without the urea step must also be performed adding to the cost and complexity to the test.

BRIEF DESCRIPTION OF THE DRAWINGS

FIG. 8 shows the correlation of the fluorescent dissociation rate results (Cy5-streptavidin-FICOLL®, Pylon) compared to the label-free BLI method. The correlation coefficient was good (r=0.87).

DETAILED DESCRIPTION OF THE INVENTION

Definitions

Figure 1:
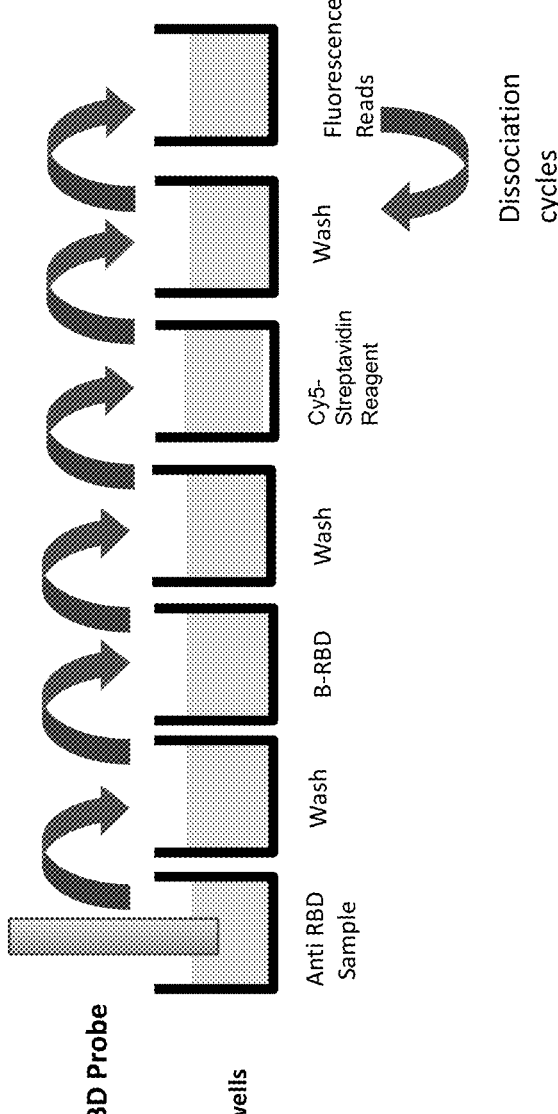
FIG. 1 depicts the assay protocol of probe transfer for measuring dissociation rate of a total antibody (including IgA, IgG, IgM, IgD). Total anti-RBD antibody is used as an illustration in FIG. 1. The probe was initially coated with an antigen (Receptor Binding Domain RBD). This assay protocol can be used for measuring dissociation rates of different antibodies by coating the probe with different antigens and using different biotylated antigens.

Terms used in the claims and specification are to be construed in accordance with their usual meaning as understood by one skilled in the art except and as defined as set forth below.

"About," as used herein, refers to within ±10% of the recited value.

"Antibody affinity" describes the strength of an antibody binds to an antigen.

"Antibody avidity" describes the measure of overall or accumulated strength of a antigen-antibody complex. It is determined by three parameters: the binding affinity of the complex, the valency of the antibody, and the structural arrangement of the antigen and the antibody in the complex that can be the cause multiple points of interaction.

An "aspect ratio" of a shape refers to the ratio of its longer dimension to its shorter dimension.

"Immobilized," as used herein, refers to reagents being fixed to a solid surface. When a reagent is immobilized to a solid surface, it is either be non-covalently bound or covalently bound to the surface.

A "probe," as used herein, refers to a substrate coated with a thin-film layer of binding molecules at the sensing side. A probe has a distal end and a proximal end. The proximal end (also refers to probe tip in the application) has a sensing surface coated with a thin layer of analyte-binding molecules. Probe can be made of glass or quartz of any other suitable materials such as plastic, optical fiber, metal, or ceramic.

This invention is directed to an immunoassay method to determine the dissociation rate of an antibody. The method has two phases: a first phase of binding and a second phase of dissociation. The first phase of the assay has a probe coated with an antigen, or protein G, or an anti-human Fc antibody. The probe is immersed in a sample containing an antibody against an antigen of interest, followed by a wash sequence, then the probe is transferred to a reagent with a biotinylated antigen. After an incubation, the antibody bound on the probe binds to the biotinylated antigen. Fluorescent signal is produced by immersing the probe in a reagent having a fluorescent tagged streptavidin. The last step is a measurement of fluorescent on the probe tip. The second phase of the assay is making subsequent fluorescent measurements over time to monitor the loss in fluorescence indicating dissociation of the immune complex and calculating the dissociation rate of the binding of the antibody to the antigen.

Fluorescent Detection System

The present invention uses a fluorescent detection system as described in U.S. Pat. No. 8,309,369, which is incorporated herein by reference, for measuring a fluorescent signal on a probe tip. The system comprises: (a) a probe having an aspect ratio of length to width at least 5 to 1, the probe having a first end and a second end, the second end having a sensing surface bound with a fluorescent label; (b) a light source for emitting excitation light directly to the probe's sensing surface; (c) a collecting lens pointed toward the sensing surface; and (d) an optical detector for detecting the emission fluorescent light; where the collecting lens collects and directs the emission fluorescent light to the optical detector.

The probe can be a monolithic substrate or an optical fiber. The probe can be any shape such as rod, cylindrical, round, square, triangle, etc., with an aspect ratio of length to width of at least 5 to 1, preferably 10 to 1. Because the probe is dipped in a sample solution and one or more assay solutions during an immunoassay, it is desirable to have a long probe with an aspect ratio of at least 5 to 1 to enable the probe tip's immersion into the solutions. Heterogeneous assays can be performed where the long probe is transferred to different reaction chambers. Dispensing and aspirating reagents and sample during the assay are avoided. The sensing surface of the probe is coated with analyte-binding molecules and bound with fluorescent labels.

Any light source that can emit proper excitation light for the fluorescent label is suitable for the present invention. A prefer light source is a laser that can emit light with wavelengths suitable for fluorescent labels. For example, the laser center wavelength is preferred to be 649 nm for Cy5 fluorescent dye. A suitable optical detector for detecting emission light is a photomultiplier tube (PMT), a charge coupled device (CCD), or a photodiode.

The light source and the optical detector including the collecting lens are mounted on the same side of the probe tip surface (the sensing surface). If the sensing surface faces down, they are both mounted below the tip surface. If the sensing surface faces up, they are both mounted above the tip surface. They are closer to the sensing surface than the other end of the probe. The sensing surface is always within the numeric aperture of the collecting lens. The probe can be, but it does not have to be centrally aligned with the collecting lens.

Methods for Determining the Dissociation Rate of an Antibody

The present invention is directed to methods of measuring the dissociation rate of the an antibody to an antigen in an antigen-antibody complex.

First Embodiment

In a first embodiment, the method measuring the dissociation rate of the an antibody to an antigen in an antigen-antibody complex. The antibody includes IgG, IgA, and IgM. In this embodiment, the probe is coated with an antigen of interest, which binds to an antibody against the antigen.

FIG. 1 depicts an assay for determining the dissociation rate of anti-COVID-19 antibody with a probe coated with receptor binding domain (RBD) antigen and a biotinylated RBD reagent. The RBD coated probe is transferred through an anti-RBD sample, followed by immersion in a biotinylated RBD (B-RBD) reagent. Anti-RBD in the sample initially binds to RBD on the probe tip and since immunoglobulins have multiple binding sites, it can form a second bond to the B-RBD in the liquid phase. The last step has the Cy5-tagged streptavidin reagent binding to any biotin on the probe surface, followed by multiple fluorescence measurements. Dissociation of antibody bound to either the RBD on the probe or B-RBD is detected in a subsequent measurements.

The method comprises the steps of: (a) obtaining a probe having an antigen immobilized on the tip of the probe, wherein the diameter of the tip surface is ≤5 mm; (b) dipping the probe tip into an antibody sample solution, wherein the antibody is specifically against the antigen; (c) dipping the probe tip into an antigen solution comprising the antigen conjugated with biotin; (d) dipping the probe tip into a signal solution comprising fluorescent labels conjugated to streptavidin, to form an immunocomplex among the antigen immobilized on the probe, the antibody, the biotinylated antigen, and the streptavidin conjugated with fluorescent labels on the probe tip; (e) dipping the probe tip into a wash solution; (f) dipping the probe tip in a first aqueous solution and measuring the first fluorescent signal of the immunocomplex emitted at the probe tip; (g) dipping the probe tip into a second aqueous solution for a period of time and then measuring the second fluorescent signal of the immunocomplex emitted at the probe tip; (h) repeating step (g) 0 to 30 times, and (i) determining the dissociation rate of the antibody based on the measured fluorescent signal change between steps (0 and (g) and the length of the period of time in step (g).

In step (a) of the present method, a probe that has a small tip is obtained. The tip has a smaller surface area with a diameter $\leq 5$ mm, preferably $\leq 2$ mm or $\leq 1$ mm. The small surface of the probe tip endows it with several advantages. In a solid phase immunoassays, having a small surface area is advantageous because it has less non-specific binding and thus produces a lower background signal. Further, the reagent or sample carry over on the probe tip is extremely small due to the small surface area of the tip. This feature makes the probe tip easy to wash, and it causes negligible contamination in the wash solution since the wash solution has a larger volume.

After each steps (b) and (c), the probe is optionally washed 1-5 times, preferably 1-3 times in a wash vessel (or a wash chamber or a wash well) containing a wash solution, for 5-30 or 5-20 seconds. This extra washing step may not be required because the amount of the carried-over solution is minimal due to a small binding surface area. The wash solution typically contains buffer and a surfactant such as Tween 20.

In steps (b), (c), and (d) of the method, the probe tip is dipped into a vessel (or a chamber or a well) for 15 seconds to 5 minutes, 15 seconds to 10 minutes, 30 seconds to 5 minutes, or 30 seconds to 10 minutes, to facilitate the binding reaction.

In step (d), the fluorescent labels in the signal solution is conjugated to streptavidin. The streptavidin is either a monomer, or the streptavidin is crosslinked to form a dimer, a trimer, a tetramer, or a multimer. Preferably, the streptavidin is linked to a high molecular weight polymer having a molecular weight of at least 1 million Daltons. The polymer in general has a molecular weight of 1,000 to 500,000 Daltons. The polymer can be a polysaccharide (e.g., dextran, amylose), a dendrimer, or a polyethylene glycol. In one embodiment, the polymer is branched and crosslinked. In one preferred embodiment, the polymer is FICOLL®.

In step (d), an immunocomplex is formed among the antigen immobilized on the probe, the antibody, the biotinylated antigen, and the streptavidin conjugated with fluorescent labels and optionally the polysaccharide polymer on the probe tip. This embodiment increases the fluorescent signal in the first-time read. In one preferred embodiment, the fluorescent labels and streptavidin are both covalently linked to a polymer.

In step (d), any suitable fluorescent label can be used. An example of a fluorescent label is an arylsulfonate cyanine fluorescent dye as described in Mujumdar et al. (1993) *Bioconjugate Chemistry,* 4:105-111; Southwick et al. (1990) *Cytometry,* 11:418-430; and U.S. Pat. No. 5,268,486. Cy5 is a preferred arylsulfonate cyanine fluorescent dye, because it has a high extinction coefficient and good quantum yield; it also has fluorescent emission spectra in a range (500 nm to 750 nm) outside of the auto-fluorescence wavelengths of most biological materials and plastics. In addition, Cy5 has a good solubility in water, and has low non-specific binding characteristics.

A fluorescent label can covalently bind to streptavidin through a variety of moieties, including disulfide, hydroxyphenyl, amino, carboxyl, indole, or other functional groups, using conventional conjugation chemistry as described in the scientific and patent literature. Exemplary techniques for binding arylsulfonate cyanine fluorescent dye labels to antibodies and other proteins are described in U.S. Pat. Nos. 5,268,486; 5,650,334; the contents of which are in incorporated herein by reference. Techniques for linking a preferred Cy5 fluorescent label to antibodies are described in a technical bulletin identified as Cat. No. A25000, published by Biological Detection Systems, Inc., Pittsburgh, Pa.

In Step (e), the probe is washed 1-5 times, preferably 1-3 times in a wash vessel containing a wash solution, for 5-30 or 5-20 seconds. The wash solution typically contains a buffer and a surfactant such as Tween 20.

In step (f), the probe stays in the wash vessel or is moved to a measurement vessel and the fluorescent signal of the bound immunocomplex is, for example, detected by the fluorescent detection system as described above, where the light source and the detector are mounted at the same side (the proximal side) of the sensing surface of the probe.

Alternatively, the methods of the present invention can be detected by other suitable fluorescent detection systems.

In step (g), the probe tip is dipped into a second aqueous solution, for a period of time and then a second fluorescent signal of the immunocomplex emitted at the probe tip is measured.

In step (h), step of (g) is optionally repeated to further disssociate the antibody from the antigen and then the fluorescent signal is measured again. Step (g) is repeated for 0-10, 2-10, 3-10, 4-10, 5-10, 5-20, 5-25, or 5-30 times, for measuring the antibody dissociation after different periods of time.

In step (i), the dissociation rate of the antibody is calculated from the measured fluorescent signals of steps (f), and (g).

In one embodiment, the binding reaction or the dissociation reaction is accelerated by agitating or mixing the solution in the vessel. For example, a flow such as a lateral flow or an orbital flow of the solution across the probe tip can be induced in one or more reaction vessels, to accelerates the binding or dissociation reaction. For example, the reaction vessels can be mounted on an orbital shaker and the orbital shaker is rotated at a speed at least 50 rpm, preferably at least 200 rpm or at least 500 rpm, such as 50-200 or 500-1,500 rpm. Additionally, the probe tip can be moved up and down and perpendicular to the plane of the orbital flow, at a speed of 0.01 to 10 mm/second, in order to induce additional mixing of the solution above and below the probe tip.

Second Embodiment

In a second embodiment, the method measuring the dissociation rate of the an IgG antibody to an antigen in an antigen-antibody complex. In this embodiment, the probe is coated with protein G, which binds to IgG-type antibodies.

Protein G is a bacterial protein from Group G Streptococci. Protein G binds to the Fc region of human $IgG_1$, $IgG_2$, $IgG_3$, and $IgG_4$ with a strong affinity of $1\times10^{-11}$, and does not bind to IgA, IgD, IgE, and IgM.

Figure 9:
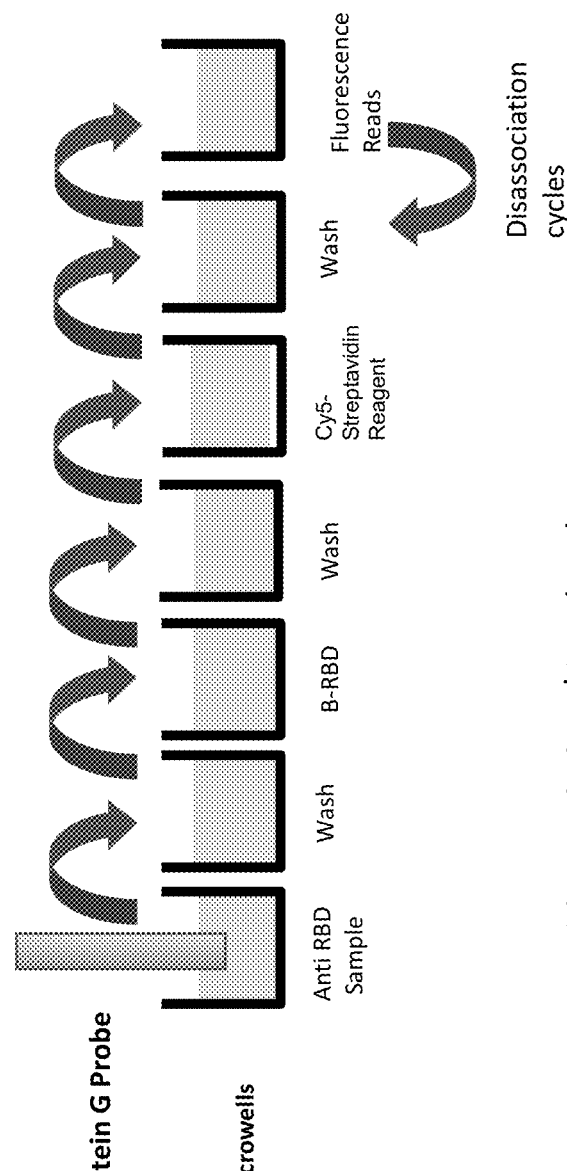
FIG. 9 depicts the assay protocol of probe transfer for measuring dissociation rate of an IgG antibody. The probe was initially coated with protein G, which binds to IgG. Anti-RBD antibody is used as an illustration in FIG. 9. This assay protocol can be used for measuring dissociation rates of different IgG antibodies by using different biotylated antigens.

FIG. 9 depicts an assay for determining the dissociation rate of an IgG antibody with a probe coated with protein G and a biotinylated RBD reagent. The protein G coated probe is transferred through an anti-RBD sample, followed by immersion in a biotinylated RBD (B-RBD) reagent. Anti-RBD IgG antibody, but not IgM or IgA antibody, in the sample initially binds to protein G on the probe tip and then it also forms a bound to the B-RBD in the liquid phase. The last step has the Cy5-tagged streptavidin reagent binding to any biotin on the probe surface, followed by multiple fluorescence measurements. Dissociation of IgG antibody bound to the B-RBD complex is detected in a subsequent measurements. Disassociation of the IgG antibody from Protein G is negligible during the time period due to the high binding affintuy of Protein G, $1\times10^{-11}$ In the second embodiment, the method comprises the steps of: (a) obtaining a probe having protein G immobilized on the tip of the probe, wherein the diameter of the tip surface is ≤5 mm; (b) dipping the probe tip into an antibody sample solution to capture IgG antibodies on the probe, wherein at least a portion of the captured IgG antibodies is specifically against an antigen of interest; (c) dipping the probe tip into a solution comprising the antigen conjugated with biotin; (d) dipping the probe tip into a signal solution comprising fluorescent labels conjugated to streptavidin, to form an immunocomplex among the protein G immobilized on the probe, the IgG antibody against the antigen, the biotinylated antigen, and the streptavidin conjugated with fluorescent labels on the probe tip; (e) dipping the probe tip into a wash solution; (f) dipping the probe tip in a first aqueous solution and measuring the first fluorescent signal of the immunocomplex emitted at the probe tip; (g) dipping the probe tip into a second aqueous solution for a period of time and then measuring the second fluorescent signal of the immunocomplex emitted at the probe tip; (h) repeating step (g) 0 to 30 times, and (i) determining the dissociation rate of the antibody based on the measured fluorescent signal change between steps (f) and (g) and the length of the period of time in step (g).

Third Embodiment

In a third embodiment, the method measuring the dissociation rate of the a total antibody to an antigen in an antigen-antibody complex. In a third embodiment, the method is similar to that of the second embodiment except protein G is replaced by a monoclonal anti-human IgG Fc antibody having a strong affinity of at least about $1\times10^{-10}$ or a polyclonal anti-human IgG Fc antibody having an average affinity of $1\times10^{-10}$. In this embodiment, the probe is coated with anti-human IgG Fc antibody or its antigen-binding fragment, for example, Fab or (Fab')$_2$.

In the third embodiment, the method comprises the steps of: (a) obtaining a probe having anti-human IgG Fc antibody or its antigen binding fragment immobilized on the tip of the probe, wherein the diameter of the tip surface is ≤5 mm; (b) dipping the probe tip into an antibody sample solution to capture IgG antibodies on the probe, wherein at least a portion of the captured IgG antibodies is specifically against an antigen of interest; (c) dipping the probe tip into a solution comprising the antigen conjugated with biotin; (d) dipping the probe tip into a signal solution comprising fluorescent labels conjugated to streptavidin, to form an immunocomplex among the anti-Fc antibody immobilized on the probe, the IgG antibody against the antigen, the biotinylated antigen, and the streptavidin conjugated with fluorescent labels on the probe tip; (e) dipping the probe tip into a wash solution; (f) dipping the probe tip in a first aqueous solution and measuring the first fluorescent signal of the immunocomplex emitted at the probe tip; (g) dipping the probe tip into a second aqueous solution for a period of time and then measuring the second fluorescent signal of the immunocomplex emitted at the probe tip; (h) repeating step (g) 0 to 30 times, and (i) determining the dissociation rate of the antibody based on the measured fluorescent signal change between steps (0 and (g) and the length of the period of time in step (g).

In the second, third, and forth embodiment, each step is similar to that described in the first embodiment, except the probe was coated with a different material for binding the sample antibody.

The invention has several advantageous aspects. The probe resides in a normal, physiologic buffer during the dissociation time period between the first and subsequent fluorescence measurements. No denaturation reagents are used to promote dissociation of the immune complex. The non-denaturing, physiologic conditions more accurately reflect the native dissociation rate of the antibody binding. Overall determination of an antibody/antigen equilibrium binding constant is a ratio of the binding on-rate and off-rate. It is typically the dissociation rate that is the prime determinant of the equilibrium binding constant, consequently a dissociation rate measurement can be used to assess avidity of antibodies in clinical samples. Dissociation rate measurements by the present invention has been validated by demonstrating similar dissociation rate ranking compared to a label-free BLI method commonly used for affinity analysis.

The second advantage of the invention is that a single probe and test reagent is used. The initial measurement quantifies the antibody binding, while the subsequent measurement enables estimation of the dissociation of the immune complex. No reference assays are required.

Lastly, the signal reagent is a fluorescent tagged-streptavidin, optionally linked to a high molecular weight polymer. The polymer is several million Daltons in molecular weight and the inventors discover that its binding to the immune complex does not perturb the avidity ranking. The polymeric signal reagent amplifies the fluorescent signal, which enables more sensitive and rapid assays.

There are several applications of the invention. It can be used to distinguish chronic versus acute infections, characterize the time course and maturation of the immune response to infectious agents, and evaluate efficacy of vaccines.

The invention is illustrated further by the following examples that are not to be construed as limiting the invention in scope to the specific procedures described in them.

EXAMPLES

Example 1. Preparation of Cy5-Streptavidin

32 μL of Cy 5-NHS (GE Healthcare) at 5 mg/ml in DMF reacted with 1 ml of streptavidin (ProZyme) at 2.4 mg/ml in 0.1 M sodium carbonate buffer pH 9.5 for 40 minutes at 30° C. Applying the mixture to a PD 10 column (GE Healthcare) removed unconjugated Cy 5. Spectral analysis indicated 2.8 Cy 5 linked per streptavidin molecule.

Example 2. Preparation of Crosslinked FICOLL® 400-SPDP

Figure 2:
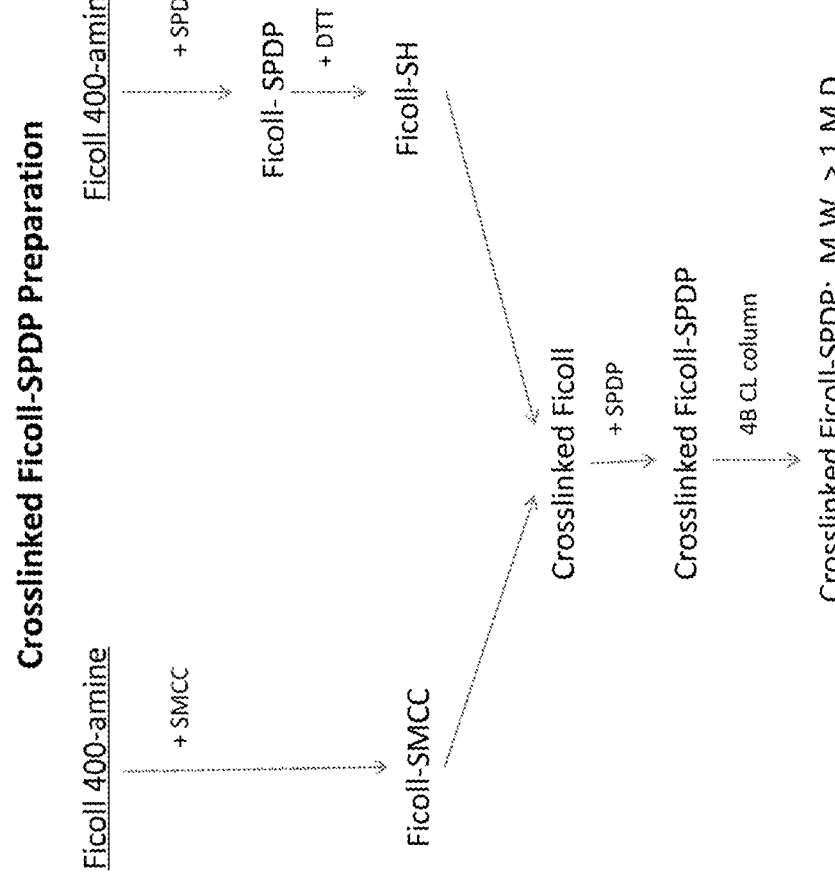
FIG. 2 depicts the crosslinked FICOLL® (copolymers of sucrose and epichlorohydrin)-SPDP preparation protocol.

Crosslinked Ficoll 400-SPDP (succinimydyl 6-[3-[2-pyridyldithio]-proprionamido]hexanoate, Invitrogen) was prepared according to Example 1 of U.S. Pat. No. 8,309,369. FIG. 2 shows a flow chart of its preparation.

Example 3. Preparation of Cy5-Streptavidin-Crosslinked FICOLL®

5.8 μL of SMCC (succinimidyl 4[N-malemidomethyl] cyclohexan-1-carboxylate) Pierce Chemical) at 10 mg/ml in DMF reacted with 2 mg Cy5-streptavidin in 1 ml PBS pH 7.4 for 1 hour at room temperature. Applying the mixture to a PD 10 column removed unbound SMCC.

The thiols on crosslinked FICOLL® 400-SPDP were deprotected by adding 30 μL DTT at 38 mg/ml to 1 mg crosslinked Ficoll 400-SPDP in 1 ml PBS and reacting for 1 hour at room temperature followed by a PD 10 column to purify the crosslinked Ficoll.

The Cy5-streptavidin-SMCC was mixed with crosslinked FICOLL® 400-SH and reacted overnight at room temperature. 104 NEM (Aldrich) at 12.5 mg/ml was then added and reacted for ½ hour at room temperature. The conjugate was then purified on a Sepharose 4B CL column. It was estimated that the conjugate carried about 20 to 30 streptavidins per Ficoll (2 million Daltons), and about 2 Cy5s per streptavidin.

Example 4. Preparation of Anti-Fluorescein Crosslinked FICOLL Conjugate

Anti-Fluorescein (Jackson Immunoresearch) at 1.5 mg/ml in 1 ml PBS was mixed with 1.9 ul SMCC at 5 mg/ml DMF and reacted for 1 hour at room temperature followed by purification on a PD 10 column. The thiols on crosslinked FICOLL® 400-SPDP were deprotected by adding 30 ul DTT at 38 mg/ml to 0.7 mg crosslinked FICOLL® 400-SPDP in 1 ml PBS and reacting for 1 hour at room temperature followed by a PD 10 column to purify the crosslinked FICOLL®.

The anti-Fluorescein-SMCC was mixed with crosslinked Ficoll 400-SH and reacted overnite at room temperature. 10 ul NEM (Aldrich) at 12.5 mg/ml was then added and reacted for ½ hour at room temperature. The conjugate was then purified on a Sepharose 4B CL column.

Example 5. RBD Labeling

RBD (SinoBIO) of Covid 19 was labeled with biotin by a standard method. RBD (SinoBIO) of Covid 19 was also labeled with a fluorescein tagged reagent by a standard method.

Example 6. RBD Probe Preparation

Quartz probes, 1 mm diameter and 2 cm in length, were coated with aminopropylsilane using a chemical vapor deposition process (Yield Engineering Systems, 1224P) following manufacturer's protocol. The probe tip was then immersed in 200 uL solutions of the following reagents in sequence. PBS (10 mM sodium phosphate, 0.15 M NaCl, pH 7.4), anti-Fluorescein (F)-FICOLL® at 30 ug/ml, PBST (PBS+0.05% Tween 20), CB (PBST+1 mg/ml BSA), F-RBD at 15 μg/ml, PBST, PPB (PBST+10% sucrose). FICOLL® was used to block non-specific binding on the probe. The probes were then placed in a convection oven at 37° C. and dried for 20 min and stored dry until assay. The probes were held stationary while the reagents wells were positioned on an orbital mixer rotating at 1000 rpm. Table 1 is shows the probe coating protocol. The coated probe is used in Examples 8 and 9.

TABLE 1

| | RBD Probe Coating Procedure | | |
| --- | --- | --- | --- |
| Step | Reagent | Shaker (rpm) | Time(s) |
| 1 | PBS | 500 | 10 |
| 2 | Anti F-Ficoll | 500 | 900 |
| 3 | CB | 500 | 60 |
| 4 | PBST | 500 | 20 |

TABLE 1-continued

| | RBD Probe Coating Procedure | | |
| --- | --- | --- | --- |
| Step | Reagent | Shaker (rpm) | Time(s) |
| 5 | F-RBD | 500 | 180 |
| 6 | PBST | 500 | 10 |
| 7 | PBST | 500 | 10 |
| 8 | PPB | 500 | 30 |

Example 7. BLI Dissociation Rate Measurements (Comparison)

Label-free, dissociation rate measurements were performed by BLI using the Gator instrument (Gator-Bio Inc.) following the manufacturer's basic procedure for kinetic analysis. Using a Gator streptavidin probe, having streptavidin coated at the tip of the BLI probe, the first step was hydrating the probe in Q buffer (PBS. 0.02% Tween 20, BSA 1 mg/ml), followed by binding B-RBD to the probe with a brief wash step. The probe was then transferred to a reagent containing anti-RBD (total antibodies). After the binding of anti-RBD to the RBD coated probe, the probe is transferred to Q buffer to monitor the dissociation of the immune complex to derive the off-rate. Table 2 shows the steps in the BLI dissociation rate assay. The avidity of total antibodies (IgG, IgM, and IgA) was determined.

TABLE 2

| | BLI Dissociation Rate Protocol (Comparison) | | |
| --- | --- | --- | --- |
| Step No. | Reagent | Time(s) | Shaker (rpm) |
| 1 | Q buffer | 60 | 1000 |
| 2 | 1 ug/ml B-RBD in Q buffer | 300 | 1000 |
| 3 | Q buffer | 120 | 1000 |
| 4 | Q buffer | 120 | 1000 |
| 5 | 10 ug/ml AB in 1002 buffer | 300 | 1000 |
| 6 | Q buffer | 900 | 1000 |

Example 8: Total Antibody Avidity with Cy5-Streptavidin Monomer as a Signal Reagent 8 anti-RBD antibodies against RBD of Covid 19 representing many variables of antibodies: monoclonal versus polyclonal, different species (human, rabbit, murine), and different immunoglobulin type, were used. Table 3 provides information on the antibodies. The assay protocol entailed adding each antibody to a concentration of 10 μg/ml in a pooled negative serum to simulate human clinical samples. Each sample was diluted 1/10 in a PBS-BSA-Tween 20 buffer, and then 120 μL antibody sample added to a micro well.

Table 4 shows the assay protocol of the present invention where the RBD coated probe is immersed in the sample and transferred through various reagents including Cy5-streptavidin monomer. The fluorescence Read steps were performed using the Pylon 3d analyzer (ET Healthcare Inc.). The Read 1 at step 16 represents the fluorescence signal of the initial immune complex serving as the 100% reference point for comparison with the later Read time points. After Read 1, the probe was transferred back to a wash well for 2 min allowing dissociation of the immune complex, and then moved back to the Read well for a subsequent fluorescence measurement. A total of seven 2-minute dissociation/read cycles were performed. The avidity of total antibodies (IgG, IgM, and IgA) was determined.

TABLE 3

Anti-RBD Antibody Panel

| AB# | Antibody name | Ref# | Lot# | Vendor |
|---|---|---|---|---|
| 1 | Anti-COVID-19 & SARS-CoV S glycoprotein monoclonal Human IgM | Ab01680-15 | T2014B01 | Absolute Antibody Ltd |
| 2 | SARS-CoV/SARS-CoV-2 Spike antibody, Chimeric Mab | 40150-D001 | HA14MA 0604 | Sino Biological Inc |
| 3 | SARS-CoV-2 (2019-nCoV) Spike RBD Antibody, Rabbit polyclonal Ab, Antigen Affinity Purified | 40592-T62 | HD14MA2002 | Sino Biological Inc |
| 4 | SARS-CoV-2 (2019-nCoV) Spike Antibody, Rabbit polyclonal Ab, Antigen Affinity Purified | 40591-T62 | HD14AP0701 | Sino Biological Inc |
| 5 | SARS-CoV-2 (2019-nCoV) Spike RBD Antibody, Rabbit polyclonal Ab, Antigen Affinity Purified | 40592-T62 | HD14AP2102 | Sino Biological Inc |
| 6 | SARS-CoV-2 (2019-nCoV) Spike Antibody, Rabbit polyclonal Ab, Antigen Affinity Purified | 40589-T62 | HD14AP0702 | Sino Biological Inc |
| 7 | SARS-CoV-2 (2019-nCoV) Spike S1 Antibody, Rabbit monoclonal Ab | 40150-R007 | MA14FE2702-B | Sino Biological Inc |
| 8 | Anti-COVID-19 & SARS-CoV S glycoprotein monoclonal Human IgG1 | Ab01680-10 | T2013B02 | Absolute Antibody Ltd |

TABLE 4

Total Anti-RBD Assay Protocol

| | Step No. | Reagent | Time(s) | Shaker (rpm) | |
|---|---|---|---|---|---|
| | 1 | PBST | 45 | 1200 | |
| | 2 | PBST | 45 | 1200 | |
| | 3 | Sample incubation | 360 | 1200 | |
| | 4 | PBST | 15 | 1200 | |
| | 5 | PBST | 15 | 1200 | |
| | 6 | PBST | 15 | 1200 | |
| | 7 | biotin-RBD | 180 | 1200 | |
| | 8 | PBST | 15 | 1200 | |
| | 9 | PBST | 15 | 1200 | |
| | 10 | PBST | 15 | 1200 | |
| | 11 | Preread | | 0 | |
| | 12 | Cy5-SA Monomer* | 30 | 1200 | Cy5-SA Monomer* or Cy5-SA-Ficoll |
| | 13 | PBST | 15 | 1200 | |
| | 14 | PBST | 15 | 1200 | |
| Initial | 15 | PBST | 15 | 1200 | |
| Immune → | 16 | Read 1 | | 0 | |
| Complex | 17 | PBST | 120 | 1200 | |
| | 18 | Read 2 | | 0 | |
| | 19 | PBST | 120 | 1200 | |
| | 20 | Read 3 | | 0 | |
| | 21 | PBST | 120 | 1200 | |
| | 22 | Read 4 | | 0 | |
| | 23 | PBST | 120 | 1200 | Dissociation/ Read Cycles |
| | 24 | Read 5 | | 0 | |
| | 25 | PBST | 120 | 1200 | |
| | 26 | Read 6 | | 0 | |
| | 27 | PBST | 120 | 1200 | |
| | 28 | Read 7 | | 0 | |
| | 29 | PBST | 120 | 1200 | |
| | 30 | Read 8 | | 0 | |

Figure 3:
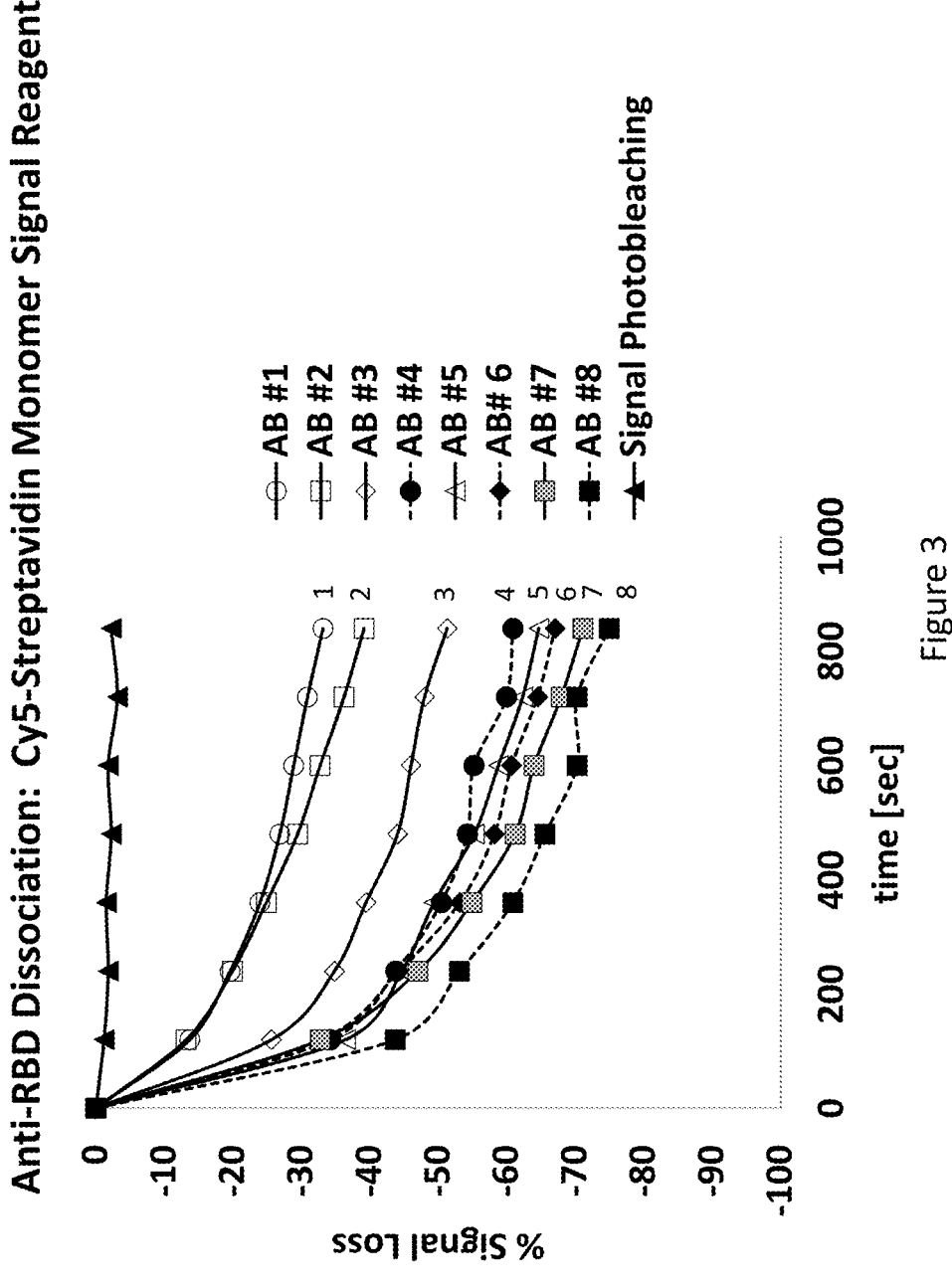
FIG. 3 shows the dissociation of 8 different anti-RBD antibody with Cy5-streptavidin monomer as a signal reagent. AB #1 is human IgM monoclonal antiboday, AB #2 is chimeric monoclonal antiboday, AB #3-6 are different rabbit polyclonal antibodies, AB #7 is rabbit monoclonal antibody, AB #8 is human IgG1 monoclonal antibody.

FIG. 3 shows the time course of dissociation of the 8 antibodies. All antibodies demonstrated dissociation curves, but to differing extents ranging from 30 to 75% loss in initial signal (Read 1). Since the dissociation steps were in the wash reagent which was PBS+Tween 20 at pH 7.4, the dissociation occurred under normal physiological conditions, and the observed dissociation was considered a reflect of the intrinsic avidity of the anti RBD antibodies.

A control ruling out photobleaching of the Cy5 dye was performed. A probe coated with biotinylated BSA was bound with the Cy5-streptavidin reagent then taken through the dissociation/Read cycles. Since streptavidin/biotin affinity is extremely high (KD~$10^{-15}$), no dissociation of the Cy5-Streptavidin was expected. The results showed that no fluorescence signal was lost with that sample, therefore, the reduced signal with the anti RBD antibody was not attributed to fluorescence decay of the Cy5.

13

Example 9: Total Antibody Avidity with Cy5-Streptavidin-FICOLL as a Signal Reagent

Figure 4:
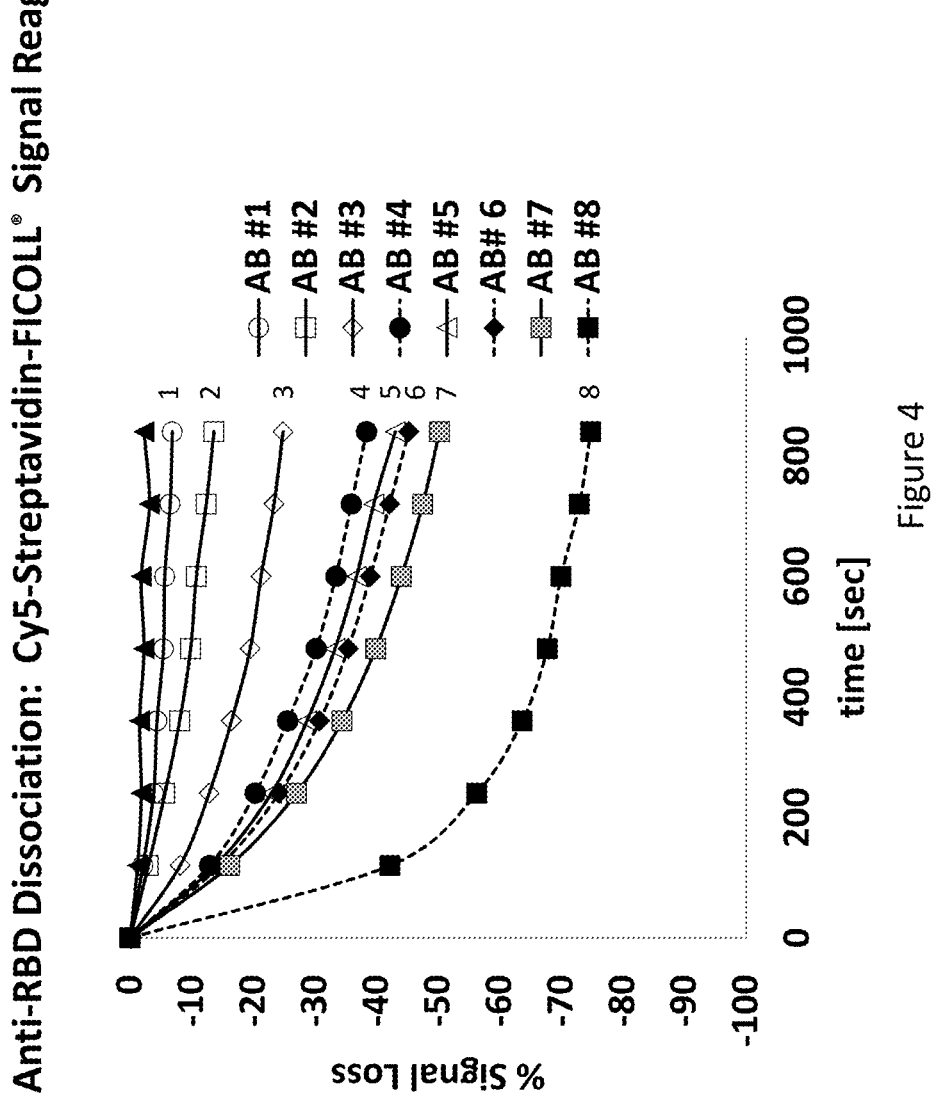
FIG. 4 shows the dissociation of 8 different anti-RBD antibody with Cy5-streptavidin-FICOLL® as a signal reagent. AB #1-8 are the same as those described above in FIG. 3.

The same 8 antibody panel was also assayed with the same protocol (see Example 8), except the Cy5-steptavidin-FICOLL® reagent was used to generate fluorescence signals. FIG. 4 shows all 8 antibodies demonstrated dissociation curves, which was remarkable in that the high molecular weight of the polymer (several million Daltons) did not interfere with the dissociation of RBD and anti-RBD. Although results with the Cy5-SA-FICOLL® (FIG. 4) had the same antibody ranking as the cy5-SA monomer (FIG. 3), the other unexpected effect was the Cy5-streptavidin-FI-COLL® produced a much broader range of dissociation compared to the Cy5-streptavidin monomer (−5 to −72% signal loss vs −30 to −75% signal loss, respectively). The broader dissociation range using Cy5-streptavidin-FI-COLL® as a signal reagent enhances the resolution of antibodies with smaller differences in dissociation rates.

Table 5 illustrates an advantage of the Cy5-Streptavidin-FICOLL®, where it generated about 10 times more fluorescence signal compared to Cy5-streptavidin monomer at Read 1. The higher signal enables detecting antibody levels at much lower concentrations.

TABLE 5

Total Anti-RBD Signals at Read 1: Cy5-Streptavidin vs Cy5-Streptavidin-FICOLL ®

| AB# | Signal with 10 μg/ml Cy5-SA-FICOLL ® | Signal with 20 μg/ml Cy5-SA monomer |
|---|---|---|
| 1 | 12084 | 1238 |
| 2 | 7057 | 546 |
| 3 | 2717 | 152 |
| 4 | 1122 | 105 |
| 5 | 571 | 85 |
| 6 | 669 | 79 |
| 7 | 3143 | 253 |
| 8 | 270 | 64 |

Figure 5:
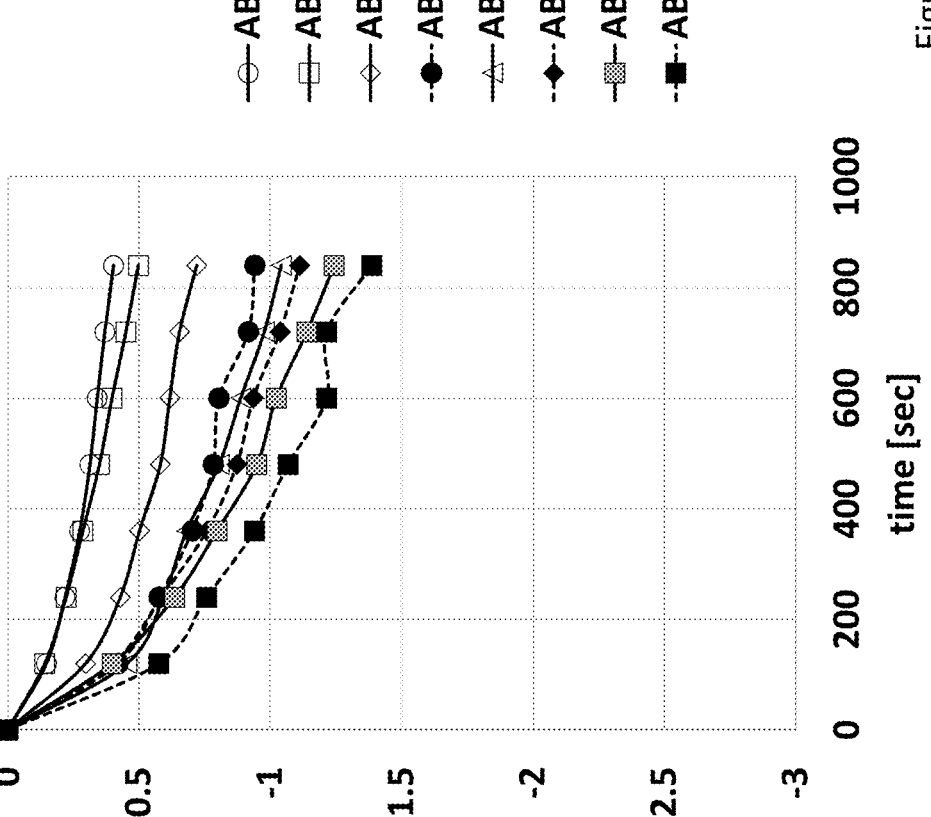
FIG. 5 illustrates the dissociation of the antibodies from the antigen-antibody complexes with Cy5-streptavidin monomer as a signal reagant, where the % signal loss was converted to log of $[Ab_x]/[Ab_0]$ to enable a calculation of dissociation rate for each antibody. $[Ab_x]$ is the antibody concentration at time x. $[Ab_0]$ is the antibody concentration at time 0, which is the time at the initial formation of the immune complex on the probe tip. Dissociation rate is the slope of $Ln$ $([Ab_x]/[Ab_0])$ vs. time, and the unit is $second^-$. The dissociation rates of the 8 antibodies (Pylon) are compared with the dissociation constants (Koff) obtained from a known label-free BLI method (Gator) in the table.

FIG. 5 illustrates the dissociation of 8 different antibodies with Cy5-streptavidin monomer as a signal reagent, where the % loss was converted to log of $[Ab_x]/[Ab_0]$ to enable a calculation of dissociation rate for each antibody.

Figure 6:
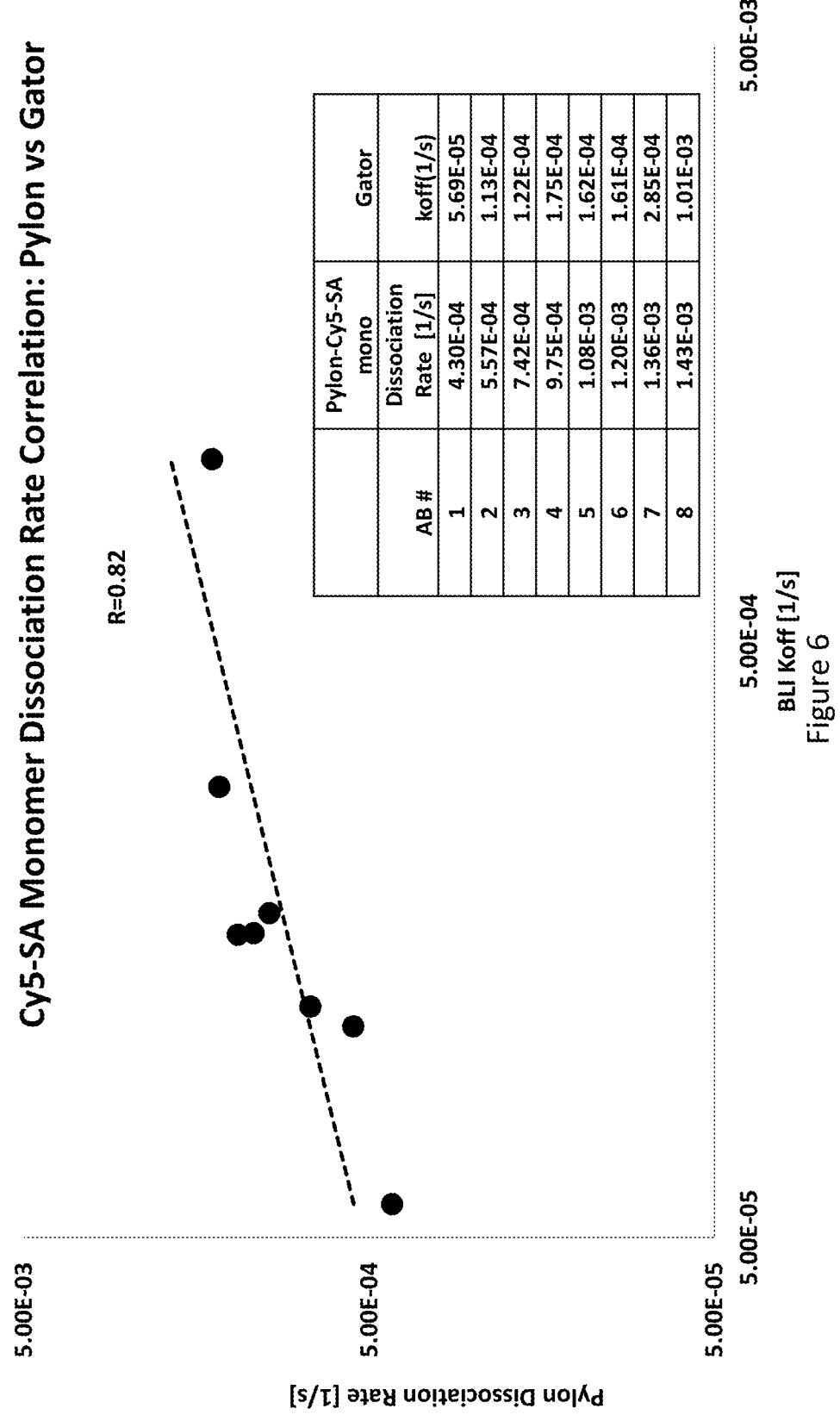
FIG. 6 shows the correlation of the fluorescent dissociation rate results (Cy5-Streptavidin monomer Signal, Pylon) compared to the label-free BLI method (Gator). The correlation coefficient was good (r=0.82).

FIG. 6 presents the correlation of the fluorescent dissociation rate results (Cy5-Streptavidin monomer as a signal reagent, Pylon) compared to the label-free BLI method (Gator). The correlation was good (r=0.82), which indicates the dissociation rate assay of the present invention can be used for antibody ranking of avidity.

14

Figure 7:
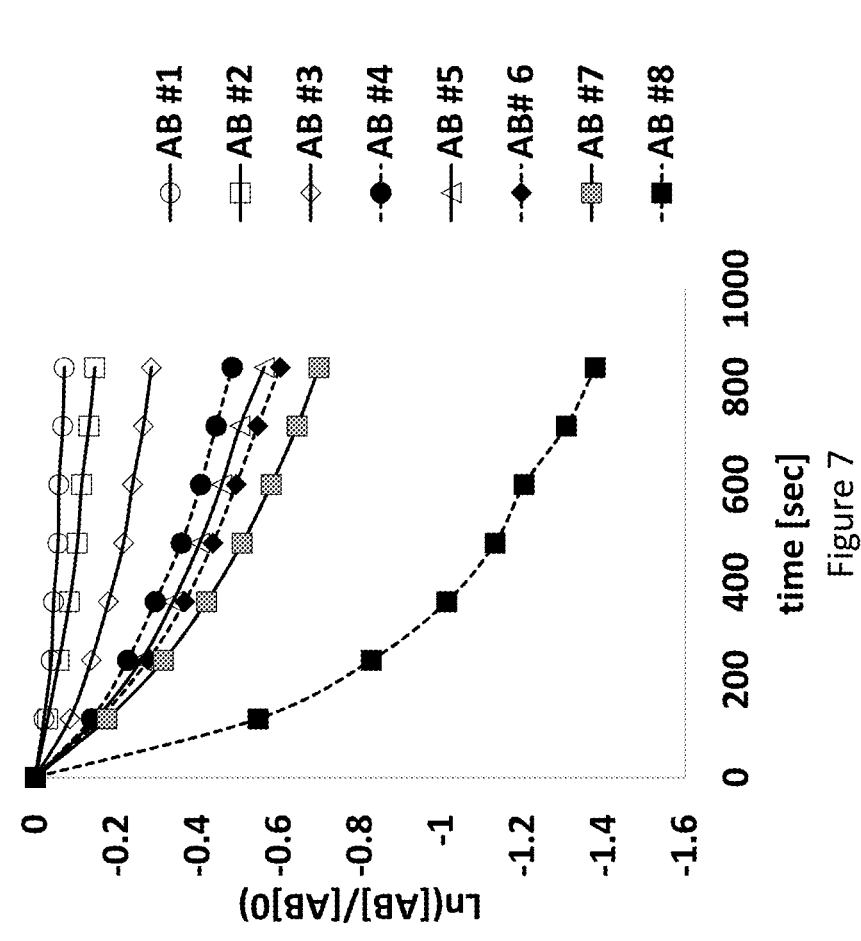
FIG. 7 illustrates the dissociation of the antibodies with Cy5-streptavidin-FICOLL® as a signal reagent, where the % loss was converted to log of $[Ab_x]/[Ab_0]$ to enable a calculation of dissociation rate for each antibody.

FIG. 7 illustrates the dissociation of the antibodies with Cy5-streptavidin-FICOLL® where the % loss was converted to log of $[Ab_x]/[Ab_0]$ to enable a calculation of dissociation rate for each antibody.

FIG. 8 presents the correlation of the fluorescent dissociation rateresults (Cy5-Streptavidin-FICOLL® Signal, Pylon) compared to the label-free BLI method. The correlation was good (r=0.85) and indicates the dissociation rate assay can be used for antibody ranking of avidity.

Example 10: Protein G-Coated Probe Preparation

Table 6 shows the protocol for preparing Protein-G coated probe.

TABLE 6

Protocol for preparing Protein G coated tube.

| Step | Reagent | Volume (μL) | Time (s) |
|---|---|---|---|
| 1 | PBS | 275 | 20 |
| 2 | Protein G (40 μg/ml) | 200 | 900 |
| 3 | Coating buffer | 275 | 180 |
| 4 | PBST Wash | 275 | 10 |
| 5 | PBST Wash | 275 | 10 |
| 6 | PBST + sucrose | 275 | 30 |

Quartz probes, 1 mm diameter and 2 cm in length, were coated with aminopropylsilane using a chemical vapor deposition process (Yield Engineering Systems, 1224P) following manufacturer's protocol. The probe tip was then immersed in 275 μL solutions of the following reagents in sequence. PBS (10 mM sodium phosphate, 0.15M NaCl, pH 7.4) for 20 sec, Protein G (Sigma Aldrich) at 40 μg/ml for 900 sec, PBST (PBS+0.05% Tween 20) Coating Buffer (PBST+1 mg/ml BSA) for 180 sec, PBST for 10 sec, PPB (PBST+10% sucrose) for 30 sec. The probes were held stationary while the reagents wells were positioned on an orbital mixer rotating at 1000 rpm at each step. The probes were then to placed in a convection oven at 37° C. and dried for 20 min and stored dry until assay. The Protein G-coated probe was used in Example 11. FIG. 9 depicts the assay protocol of probe transfer for measuring dissociation rate of an anti-RBD antibody using the protein G coated probe.

Example 11: IgG Antibody Avidity with Cy5-Streptavidin-Ficoll Signal Reagent

FIG. 9 depicts the assay protocol of probe transfer for measuring dissociation rate of an anti-RBD antibody using the protein G coated probe of Example 10. The details of the assay protocol is shown in Table 7.

TABLE 7

IgG Anti-RBD Assay Protocol

| Step No. | Reagent | Time(s) | Shaker (rpm) |
|---|---|---|---|
| 1 | PBST | 45 | 1200 |
| 2 | PBST | 45 | 1200 |
| 3 | Sample incubation | 360 | 1200 |
| 4 | PBST | 15 | 1200 |
| 5 | PBST | 15 | 1200 |
| 6 | PBST | 15 | 1200 |
| 7 | biotin-RBD | 180 | 1200 |
| 8 | PBST | 15 | 1200 |
| 9 | PBST | 15 | 1200 |
| 10 | PBST | 15 | 1200 |

TABLE 7-continued

IgG Anti-RBD Assay Protocol

| | Step No. | Reagent | Time(s) | Shaker (rpm) | |
|---|---|---|---|---|---|
| | 11 | Preread | | 0 | |
| | 12 | Cy5-SA Ficoll | 30 | 1200 | |
| | 13 | PBST | 15 | 1200 | |
| | 14 | PBST | 15 | 1200 | |
| Initial | 15 | PBST | 15 | 1200 | |
| Immune → | 16 | Read 1 | | 0 | |
| Complex | 17 | PBST | 120 | 1200 | |
| | 18 | Read 2 | | 0 | |
| | 19 | PBST | 120 | 1200 | |
| | 20 | Read 3 | | 0 | |
| | 21 | PBST | 120 | 1200 | |
| | 22 | Read 4 | | 0 | |
| | 23 | PBST | 120 | 1200 | Dissociation/ |
| | 24 | Read 5 | | 0 | Read Cycles |
| | 25 | PBST | 120 | 1200 | |
| | 26 | Read 6 | | 0 | |
| | 27 | PBST | 120 | 1200 | |
| | 28 | Read 7 | | 0 | |
| | 29 | PBST | 120 | 1200 | |
| | 30 | Read 8 | | 0 | |

Figure 10:
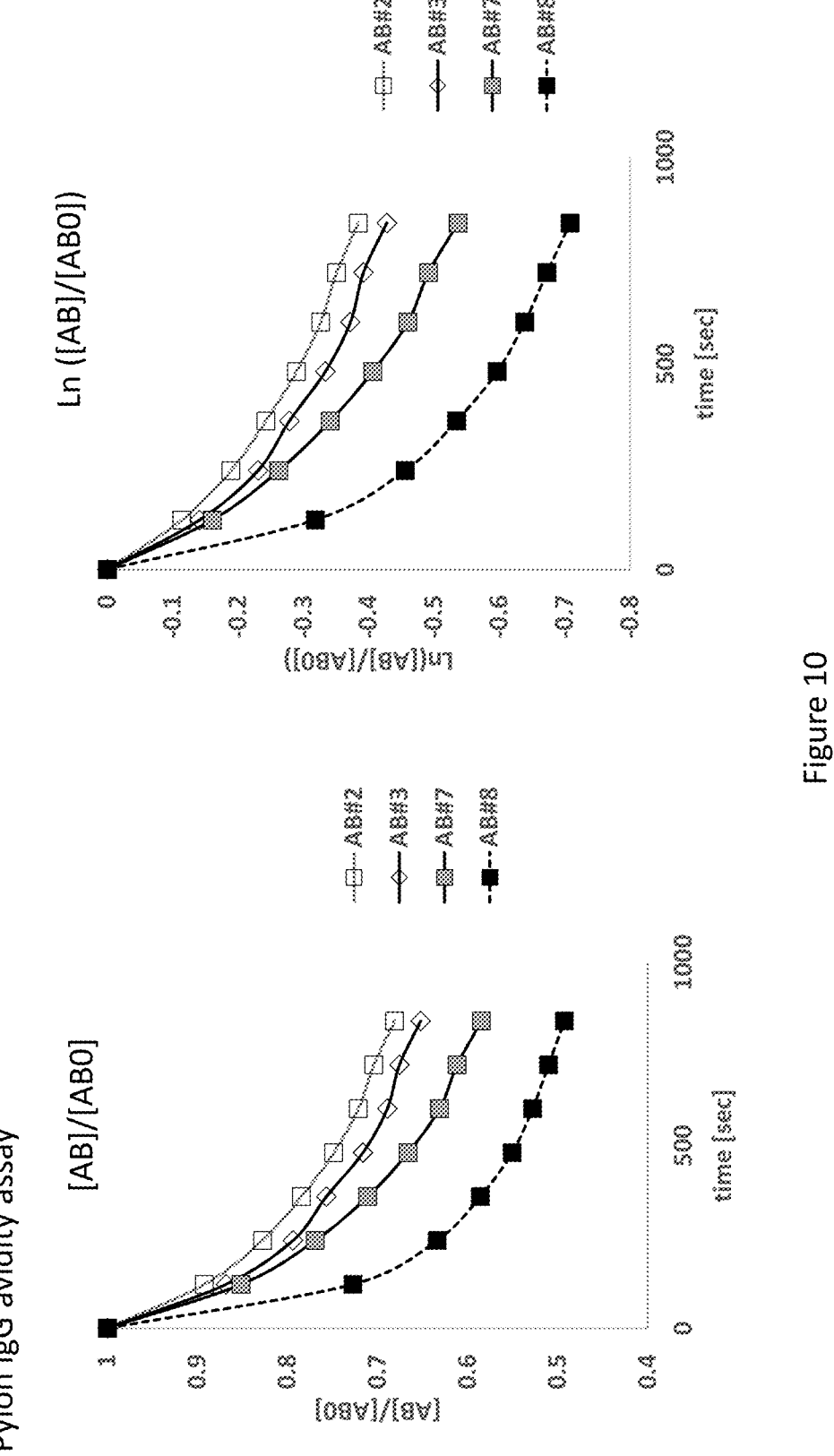
FIG. 10 shows the dissociation curves with four human anti-RBD IgG antibodies. The source of the four antibodies are shown in Table 10.

Diassociation rates of several human anti-RBD antibodies was determined using Protein G probes with the protocol described in Table 7. FIG. 10 presents the dissociation curves with the human anti-RBD IgG antibodies. Table 8 shows the dissociation rates (dR Pylon, Invention) calculated by curve fitting compared the Koff rates (Gator, Comparison) derived the a Gator BLI instrument. A similar ranking of dissociation rate of Pylon vs Koff of Gatir is achieved.

TABLE 8

Dissociation rate of Pylon vs. Gator (comparison)

| AB# | Koff(1/s) Gator Comparison | dR Pylon IgG assay (1/s) | Antibody | Ref# | lot# | Vendor |
|---|---|---|---|---|---|---|
| 2 | 1.13E−04 | 4.30E−04 | Chimeric S1 MAB | 40150-D001 | HA14MA0604 | SinoBiological |
| 3 | 1.22E−04 | 4.69E−04 | Rab RBD PAB | 40592-T62 | HD14MaA2002 | SinoBiological |
| 7 | 2.85E−04 | 6.02E−04 | Rab S1 MAB | 40150-R007 | MA14FE270s-B | SinoBiological |
| 8 | 1.01E−03 | 7.29E−04 | Hu IgG$_1$ MAB | Ab01680-10 | T2013B02 | Absolute Antibody |

*MAB refers to monoclonal antibody. PAB refers to polyclonal antibody

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method of measuring the dissociation rate of the binding of an antibody to an antigen, comprising the steps of:

(a) obtaining a probe having an antigen immobilized on the tip of the probe, wherein the diameter of the tip surface is ≤5 mm;

(b) dipping the probe tip into an antibody sample solution, wherein the antibody is specifically against the antigen;

(c) dipping the probe tip into an antigen solution comprising the antigen conjugated with biotin;

(d) dipping the probe tip into a signal solution comprising fluorescent labels conjugated to streptavidin, to form an immunocomplex among the antigen immobilized on the probe, the antibody, the biotinylated antigen, and the streptavidin conjugated with fluorescent labels on the probe tip;

(e) dipping the probe tip into a wash solution;

(f) dipping the probe tip in a first aqueous solution and measuring the first fluorescent signal of the immunocomplex emitted at the probe tip;

(g) dipping the probe tip into a second aqueous solution for a period of time and then measuring the second fluorescent signal of the immunocomplex emitted at the probe tip;

(h) repeating step (g) 0 to 30 times, and (i) determining the dissociation rate of the antibody based on the measured fluorescent signal change between steps (f) and (g) and the length of the period of time in step (g).

2. The method of claim 1, wherein step (d), the signal solution comprises fluorescent labels conjugated to streptavidin and a branched and crosslinked polysaccharide polymer having a molecular weight of at least 1 million Daltons, to form an immunocomplex among the antigen immobilized on the probe, the antibody, the biotinylated antigen, and the streptavidin conjugated with fluorescent labels and the polysaccharide polymer on the probe tip.

3. The method according to claim 2, wherein the polysaccharide is a copolymer of sucrose and epichlorohydrin.

4. The method according to claim 1, wherein the fluorescent labels are arylsulfonate cyanines.

5. The method according to claim 4, wherein the arylsulfonate cyanine is Cy5.

6. The method according to claim 1, wherein the probe has an aspect ratio of length to width at least 5 to 1.

7. The method according to claim 1, wherein the diameter of the tip surface is ≤about 2 mm.

8. The method according to claim 1, wherein the antibody is an anti-COVID-19 antibody.

9. A method of measuring the dissociation rate of the binding of an IgG antibody to an antigen of interest, comprising the steps of:

(a) obtaining a probe having protein G, or an anti-IgG Fc antibody immobilized on the tip of the probe, wherein the diameter of the tip surface is ≤5 mm;

(b) dipping the probe tip into an antibody sample solution to capture IgG antibody in the antibody sample solution on the probe, wherein at least a portion of the captured IgG antibody is specifically against the antigen of interest;

(c) dipping the probe tip into a solution comprising the antigen conjugated with biotin;

(d) dipping the probe tip into a signal solution comprising fluorescent labels conjugated to streptavidin, to form an immunocomplex among (i) the protein G or anti-IgG Fc antibody immobilized on the probe, (ii) the IgG antibody against the antigen, (iii) the biotinylated antigen, and (iv) the streptavidin conjugated with fluorescent labels on the probe tip;

(e) dipping the probe tip into a wash solution;

(f) dipping the probe tip in a first aqueous solution and measuring the first fluorescent signal of the immunocomplex emitted at the probe tip;

(g) dipping the probe tip into a second aqueous solution for a period of time and then measuring the second fluorescent signal of the immunocomplex emitted at the probe tip;

(h) repeating step (g) 0 to 30 times, and (i) determining the dissociation rate of the antibody based on the measured fluorescent signal change between steps (f) and (g) and the length of the period of time in step (g).

10. The method of claim 9, wherein step (d), the signal solution comprises fluorescent labels conjugated to streptavidin and a branched and crosslinked polysaccharide polymer having a molecular weight of at least 1 million Daltons, to form an immunocomplex among the antigen immobilized on the probe, the antibody, the biotinylated antigen, and the streptavidin conjugated with fluorescent labels and the polysaccharide polymer on the probe tip.

11. The method according to claim 2, wherein the polysaccharide is a copolymer of sucrose and epichlorohydrin.

12. The method according to claim 10, wherein the fluorescent labels are arylsulfonate cyanines.

13. The method according to claim 12, wherein the arylsulfonate cyanine is Cy5.

14. The method according to claim 9, wherein the probe has an aspect ratio of length to width at least 5 to 1.

15. The method according to claim 9, wherein the diameter of the tip surface is ≤about 2 mm.

16. The method according to claim 9, wherein the antibody is an anti-COVID-19 antibody.

17. The method according to claim 9, wherein the IgG antibody is an human IgG antibody, and the anti-IgG Fc antibody is an anti-human Fc antibody.

* * * * *